United States Patent [19]
Hideo et al.

[11] Patent Number: 5,919,770
[45] Date of Patent: Jul. 6, 1999

[54] METABOLITES OF GINSENG SAPONINS BY HUMAN INTESTINAL BACTERIA AND ITS PREPARATION FOR AN ANTICANCER

[75] Inventors: Hasegawa Hideo, Tokyo, Japan; Jong Hwan Sung, Guri-si, Rep. of Korea; Matsumiya Satoshi; Uchiyama Masamori, both of Tokyo, Japan; Jae Doo Huh, Guri-si, Rep. of Korea

[73] Assignees: Il Hwa Co., Ltd., Guri-si, Rep. of Korea; Happy World Inc., Tokyo, Japan

[21] Appl. No.: 08/945,422

[22] PCT Filed: Dec. 31, 1996

[86] PCT No.: PCT/KR96/00281

§ 371 Date: Oct. 22, 1997

§ 102(e) Date: Oct. 22, 1997

[87] PCT Pub. No.: WO97/31013

PCT Pub. Date: Aug. 28, 1997

[30] Foreign Application Priority Data

Feb. 22, 1996 [KR] Rep. of Korea ............... 1996/4217

[51] Int. Cl.$^6$ ............... A61K 31/58; C07J 17/00
[52] U.S. Cl. ............... 514/26; 514/171; 514/172; 514/182; 536/6
[58] Field of Search ............... 514/26, 182, 171, 514/172; 536/6

[56] References Cited

PUBLICATIONS

Biol. Pharm. Bull., 17(5), pp. 635–639 (1994).
Chem. Pharm. Bull., 20(11), pp. 2418–2421 (1972).
Tetrahedron, 27, pp. 881–892 (1971).
Planta Med., 60, pp. 240–243 (1994).
Planta Med., 61, pp. 409–413 (1995).
Phytotherapy Res., 9, pp. 260–263 (1995).

Chemical abstracts, vol. 124, (Columbus, Ohio, USA), abstact No. 283952, J.H.Sung et al, "Metalbolism of Ginseng Saponins by Human Intestinal Bacteria", & Saengyak Hakhoechi, 1995, 26(4), 360–7.

*Primary Examiner*—Richard L. Raymond
*Attorney, Agent, or Firm*—Jacobson, Price, Holman & Stern PLLC

[57] ABSTRACT

This invention relates to ginsenoside Mc with formula (I),

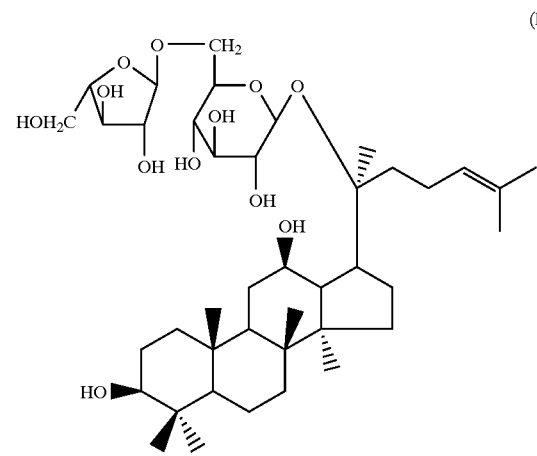

an intestinal flora metabolite of ginseng saponin and anticancer agent containing it as an active ingredient. In addition to a novel compound, the anticancer agent of this invention consists of one active ingredient elected from compound K, compound Y or 20(S)-protopanaxatriol, intestinal flora metabolites of ginseng saponin, together with one or more pharmaceutically acceptable carriers. Said agent is a novel type of potential anticancer agent since it has immunopotentiating actions including inhibitory actions on the vascularization of tumors and extravasation of cancer cells.

16 Claims, No Drawings

METABOLITES OF GINSENG SAPONINS BY HUMAN INTESTINAL BACTERIA AND ITS PREPARATION FOR AN ANTICANCER

The present application is a 371 of PCT/KR96/00281, filed Dec. 31, 1996.

FIELD OF THE INVENTION

This invention relates to the metabolites of ginseng saponins by human intestinal bacteria and its preparation for an anticancer and more particularly, to a novel saponin of a metabolite of Panax ginseng saponin by human bacteria and a novel preparation of anticancer agent containing a novel saponin of a metabolite of Panax ginseng saponin by human bacteria, which exhibits immunopotentiating actions including inhibitory actions on the vascularization of tumors and extravasation of cancer cells.

DESCRIPTION OF THE RELATED ART

In recent years much of the development of novel anticancer agents has widely focused on natural sources and synthetic compounds.

Among saponins extracted from Panax ginseng, for example, ginsenoside $Rh_2$ [3-0-β-D-glucopyranosyl-20(s)-protopanaxadiol] was reported to inhibit the proliferation of liver cancer cells (reference: Japanese Patent No. 89-28759).

Further, both ginsenoside $Rg_3$ [3-0-[β-D-glucopyranosyl (1→2)-β-D-glucopyranosyl]-20(R)-protopanaxadiol] and ginsenoside $Rb_2$[20-0-[α-L-arabinopyranosyl(1→6)-β-D-glucopyranosyl-3-0-[β-D-glucopyranosyl(1→2)-β-D-glucopyranosyl]-20(S)-protopanaxadio 1] were reported to inhibit the vascularization of tumors and extravasation of cancer cells including inhibitory actions on the metastatis of cancer cells [References: Japanese Patent No. 93-9123, Sato et al.: Biol. Pharm. Bull., 17. 635(1994)].

In case of 20-0-β-D-glucopyranosyl]-20(S)-protopanaxadiol, called as "compound K" and 20-0-[α-L-arabinopyranosyl (1→6)-β-D-glucopyranosyl]-20(S)-protopanaxadiol, called as "compound Y", which were isolated from soil strains of Panax ginseng saponin and intestinal flora of rats, their structure was already determined [References: Yoshioka et al.: Chem. Pharm. Bull., 20, 2418 (1972), Takino et al.: Medicinal ginseng '69 (Public Publishing Co., Ltd. 267(1989)].

Also, the structure of 20(S)-protopanaxatriol, isolated by sapogenin of Panax ginseng saponin, was already established (Nagai et al.: Tetrahedron, 27, 881(1971)].

The pharmacological actions of these compounds, for example, inhibition of glucose transplant related to cancer cells by the blockage of membrane protein, were merely reported by each inventor [Hasegawa et al., Planta Med., 60, 197(1994)], including the report on methicillin-resistant bacteria and the inhibition of the excretion of drugs on the multidrugs-resistant cancer cells [Hasegawa et al.: Phytother, Res., 9, 260(1996), Hasegawa et al., Planta Med., 61, 409(1995)].

In case of the conventional chemotherapeutics which exhibit their therapeutic effects by attacking the cancer cells directly, their adverse effects are quite severe. During several decades, any antineoplastic agents with new mode of mechanism have not yet to be on the market. Further, in the event that Panax ginseng saponins are applied for the treatment of some diseases, these substances are reported to be metabolized by intestinal bacteria and said bacteria is liable to be influenced by human's constitution and his food pattern. Thus, any individual differences in the metabolism of sanponins may lead to the individual differences in his treatment.

SUMMARY OF THE INVENTION

In view of these situations, the inventors of this invention have investigated the metabolism of ginseng saponin associated by human intestinal bacteria and succeeded in isolating and identifying the following compounds, i.e., a) protopanaxadiol saponins(ginsenoside $Rb_1$, ginsenoside $Rb_2$ and ginsenoside Rc), b) compound K, compound Y and 20-0-[α-L- arabinofuranosyl(1→6)-β-D-glucopyranosyl-20 (S)-protopanaxadiol], which are called as ginsenoside Mc. metabolites of ginsenoside Rd, and c) 20(S)-protopanaxatriol, a metabolite of ginsenoside $Rg_1$ and ginsenoside Re which belongs to protopanaxatriol saponin.

The inventor ascertains that these intestinal flora metabolites are absorbed from intestinal tracts to blood and excreted via urine and feces. By assuring that said intestinal flora metabolites prove to be main substances of Panax ginseng saponin, the inventor has endeavored to develop the therapeutic dosage form containing the active ingredient of saponin, which is not influenced by the difference of intestinal bacteria. As a result of reviewing these physiological activities, the inventor has discovered a novel preparation of anticancer agent, which exhibits immunopotentiating actions including inhibitory actions on the vascularization of tumors and extravasation of cancer cells. Thus, this invention has finally completed.

Therefore, the object of this invention is to provide a new compound of 20-0-[α-L-arabinofuranosyl(1→6)-β-D-glucopyranosyl-20(S)-protopanaxadiol] having the following formula, a novel ginseng saponin metabolite by human intestinal bacteria(called as ginsenoside Mc) with the following characteristics.

1) Structural fomula

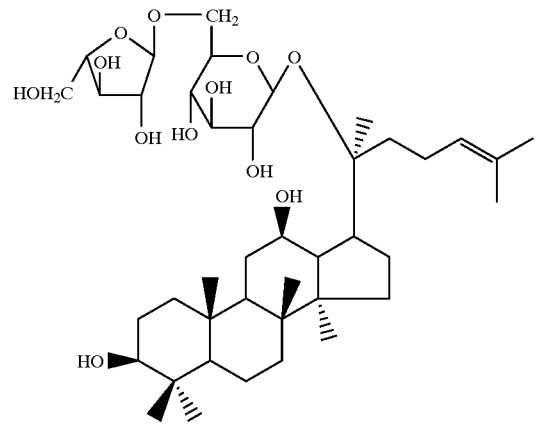

2) Molecular formula: $C_{41}H_{70}O_{12}$

3) The mass spectrum (Fab-MS, negative and m/z) showed signals at 753[M-H]⁻, 621(M-arabinofuranose-H]⁻, and 459[M-arabinofuranos-glucopyranos-H]⁻.

4) The $^1$H-NMR spectrum(d5-pyridine) showed signals at δ 3.39(1H, t, J=10.5, 5.1 Hz, H-3), 0.80(1H, d, J=11.0 Hz, H-5), 3.93(1H, ddd-like, H-12), 5.32(1H, t, J=7.1 Hz, H-24), 0.92(3H, s, Me-18), 0.89(3H, s, Me-19), 1.69(3H, s, Me-21), 1.67(3H, s, Me-26), 1.67(3H, s, Me-27), 1.21(3H, s, Me-28), 1.01(3H, s, Me-29), 0.99(3H, s, Me-30), 5.10(1H, d, J=7.8 Hz, H-1'-20-glucopyranosyl), 5.61(1H, J=1.7 Hz, H-1"-6'-arabinofuranosyl).

5) The $^{13}$C-NMR spectrum(d5-pyridine) for aglycon moiety showed signals at δ39.5(C-1), 28.3(C-2), 78.2(C-3), 39.5(C-4), 56.5(C-5), 18.8(C-6), 35.2(C-7), 40.2(C-8), 50.4 (C-9), 37.4(C-10), 30.8(C-11), 70.3(C-12), 49.5(C-13), 51.5 (C-14), 30.9(C-15), 26.7(C-16), 51.8(C-17) 16.3(C-18), 16.1(C-19), 83.2(C-20), 22.4(C-21), 36.2(C-22), 23.2(C-23), 126.1(C-24), 131.0(C-25), 25.8(C-26), 17.9(C-27), 28.7(C-28), 16.4(C-29), 17.5(C-30), The $^{13}$C-NMR spectrum(d5-pyridine) for 20-glucopyranosyl moiety showed signals at 98.1(C-1'), 75.1(C-2'), 79.2(C-3'), 72.2(C-4'), 76.5(C-5'), 68.5(C-6'), The $^{13}$C-NMR spectrum(d5-pyridine) for 6'-arabinofuranosyl moiety showed signals at 110(C-1"), 83.5(C-2"), 79.0(C-3"), 86.3(C-4"), 62.8(C-5").

In addition to ginsenoside compound Mc, a novel intestinal bacteria metabolite of novel ginseng saponin, another object of this invention is to provide an anticancer agent containing one active ingredient selected from intestinal bacteria metabolites of ginseng saponin such as compound K, compound Y, ginsenoside Mc and protopanaxatriol, together with one or more pharmaceutically acceptable carriers. These intestinal bacteria metabolites of ginseng saponin exhibits remarkable antineoplastic effects in the long run since they potentiate the inhibitory actions against cancer cells in lymphocyte and inhibit the vascularization of tumors and extravasation of cancer cells.

Even though the severity of symptoms differs, the oral dose of anticancer agent for adult according to this invention is 1–50 mg/60 kg of body weight once daily or several times per a day, preferably 3–15 mg/day/60 kg of body weight.

The anticancer agent according to this invention contains either a single ingredient, or said ingredient plus one or more pharmaceutically acceptable carriers such as excipients in the form of solid or liquid.

The administration method and available dosage forms are as follows;

a) Oral forms: powders, tablets, suspensions, emulsifiers, capsules, granules, troches, pills, suspensions, spirits, syrups and limonades;

b) Injectable forms, or c) Topical forms: ointments, solids, suspensions, powders, paps, suppositories, aerosols, cataplasmas, liniments, lotions, enemas and emulsifiers.

According to this invention, well-known excipients in the form of solid or liquid may be used As mentioned in the above, the formulation should be conducted so as to contain the active ingredient of this invention necessary for single dose. The several examples of excipients used in related dosage forms are as follows:

Excipients in powders and other oral powders: lactose, crystalline cellulose, starch, dextrin, calcium phosphate, calcium carbonate, synthetic and natural aluminum dioxide, magnesium oxide, dried aluminum hydroxide, magnesium stearate, and sodium bicarbonate;

Excipients in topical powders: zinc oxide, talc, starch, kaolin, borate powder, zinc stearate, magnesium stearate, magnesium carbonate, precipitated calcium carbonate, bismuth subgallate, and potassium aluminum sulfate powder;

Excipients in liquids: water, glycerin, propylene glycol, sweet-taste syrup, ethanol, fatty oil, ethylene glycol, polyethylene glycol, and sorbitol;

Excipients in ointments: hydrophobic or hydrophilic base (including oil-soluble base, water-soluble base and suspended base) prepared by mixing fat, fatty oil, lanoline, vaseline, glycerin, wax, Japan wax, paraffin, paraffin sulfate, resins, higher alcohols, plastics, glycols, water, or surfactant.

EXAMPLE

Preparation of ginsenoside Mc

The suspended solution of human flora was precultured in GAM medium overnight and then,100 mg of ginsenoside Rc was added to said medium to the desired concentration of 2% in a newly sterile GAM medium and then cultured at 37° C. for 1 day. The medium was extracted by 1-butanol and the extracted solution was concentrated and purified on reversed/irreverse phase chromatography to give 25 mg of pure ginsenoside Mc.

[Formulation example]

Formulation example 1: A mixture of lactose, crystalline cellulose and 1% magnesium stearate was added to 30 mg of compound K, an intestinal flora metabolite of ginseng saponin, for homogenous mixing. Said mixture was tabletted by a tabletting machine to obtain each tablet containing 200 mg.

Formulation examples 2~4: Based upon the same procedure as described in formulation 1, each preparation was obtained containing 30 mg of compound Y, ginsenoside Mc or 20(S)-protopanaxatriol, respectively, instead of 30 mg of compound K.

Formulation example 5: A solution of 15 mg of compound K, an intestinal flora metabolite of ginseng saponin and polysorbit 80 was filled into a sterilized vial aseptically and after removing the moisture, the preparation for injection was obtained.

Formulation example 6~8: Based upon the same procedure as described in formulation 5, each preparation was obtained containing 15 mg of compound Y, ginsenoside Mc or 20(S)-protopanaxatriol, respectively, instead of 15 mg of compound K.

The physiological actions involved in the intestinal flora metabolite of ginseng saponin of this invention are described in the following examples but these protective scopes are not confined to said examples.

[Experiment 1]

Antitumor activity on leukemia cell line (P388) in lymphocyte of mice a) Experimental method Spleen lymphocytes of mice and leukemia cell line (P388) were used for this experiment. Spleen lymphocytes ($4\times10^6$ cells) and leukemia cells (P388) ($2\times10^8$ cells) were cultured in a medium (RPMI 1640 supplemented with 20 $\mu$M mercaptoethanol and 10% fetal bovine serum) containing intestinal flora metabolite of ginseng saponin (2.5 $\mu$M) in 5% $CO_2$ saturated with steam for 16 hours. Aside from this, same numbers of spleen lymphocytes or leukemia cell line were cultured in a medium containing intestinal flora metabolite of ginseng saponin in same is concentration as a control. The number of each survived cell was purified by MTT method to calculate impaired rate of cells on leukemia cells (P388) of lymphocytes.

b) Experimental results

As shown in table 1, the experimental results revealed that all intestinal flora metabolites of ginseng saponin in a low concentration of 2.5 $\mu$M exhibited antitumor activities 1.6 to 2 times as higher as control group.

TABLE 1

Antitumor activity on the cancer cells of lymphocyte by intestinal flora metabolites of ginseng saponin

|  | Concentration ($\mu$g/ml) | Antitumor activity (%) |  |
| --- | --- | --- | --- |
| Control |  | 31.3 | 1 |
| Compound K | 1.56 | 51.5 | 1.6 |

TABLE 1-continued

Antitumor activity on the cancer cells of lymphocyte
by intestinal flora metabolites of ginseng saponin

|  | Concentration ($\mu$g/ml) | Antitumor activity (%) |  |
|---|---|---|---|
| Compound Y | 1.86 | 56.6 | 1.8 |
| Ginsenoside Mc | 1.86 | 63.3 | 2.0 |
| 20(S)-protopanaxatriol | 1.19 | 82.4 | 2.0 |

[Experiment 2]

Inhibition on the vascularization of tumor (Test for the inhibition on the proliferation)

a) Experimental method

Human lymphocyte (HL), leukemia cell line (K562) and bovine artery endotheliocyte (BAE) were used for this experiment. HL ($1 \times 10^5$ cells), leukemia cell line (K562) ($2 \times 10^5$ cells) and BAE ($5 \times 10^3$ cells) were cultured in a medium (HL, K562: RPMI 1640 medium containg 10% fetal bovine, BAE: DMEM medium containing 10% fetal bovine) containing intestinal flora metabolites of ginseng saponin concentrated with 2-fold dilution in 5% $CO_2$ saturated with steam (HL, K562: 24 hours, BAE: 72 hours). The number of each survived cell was purified by MTT method to calculate 50% inhibition concentration ($IC_{50}$), impaired rate of cells ($IC_{50}$(HL)/$IC_{50}$(BAE) and $IC_{50}$(K562)/$IC_{50}$(BAE).

b) Experimental results

As shown in table 2, the experimental results revealed that ginsenoside, Mc and 20(S)-protopanaxatriol exhibited inhibitory activities on the proliferation of tumor cells

TABLE 2

Inhibitory activity on the proliferation by
intestinal flora metabolites of ginseng saponin

|  | $IC_{50}$ ($\mu$M) | | | $IC_{50}$ (C)/$IC_{50}$ (BAE) | |
|---|---|---|---|---|---|
|  | HL | K562 | BAE | C = HL | K562 |
| Compound K | 45 | 26 | 28 | 1.7 | 1.6 |
| Compound Y | 83 | 78 | 32 | 2.6 | 2.6 |
| Ginsenoside Mc | 220 | 480 | 26 | 8.5 | 18 |
| 20(S)-protopanaxatriol | 280 | 49 | 36 | 7.8 | 1.4 |

[Experiment 3]

Inhibition on the vascularization of tumor (Test for the inhibition on the migration)

a) Experimental method

Bovine artery endotheliocyte (BAE) was used for this experiment. BAE ($5 \times 10^3$ cells) was cultured in 6-well plate for 24 hours and cells attached to the plate were detached by a razor. Said medium was replaced by a new one and after one hour, a solution of intestinal flora metabolite of ginseng saponin was added to the desired inhibitory concentration of 10% and 50%, respectively for 24-hour cultivation. After completing the cultivation, cells were fixed with methanol, stained with Giemsa method and counted the cells migrated from the detached line under microscope.

b) Experimental results

As shown in table 3, the experimental results revealed that each intestinal metabolite of ginseng saponin exhibited an inhibitory activity of migration and among them, it was noted that compound K showed more potent inhibitory activity of migration than Suramin (Wako Pure Chem Ind. Ltd., Japan), a control group.

TABLE 3

Migration-inhibition by intestinal flora metabolites of ginseng saponin

|  | Migration-inhibition (% control) | |
|---|---|---|
|  | $IC_{10}$ | $IC_{50}$ |
| Suramin | −3.8 | 37.1 |
| Compound K | 4.6 | 43.2 |
| Compound Y | −3.7 | 28.9 |
| Ginsenoside Mc | −1.6 | 30.0 |
| 20(S)-protopanaxatriol | −1.6 | 30.0 |

[Experiment 4]

Inhibition on the extravasation of basement membrane a) Experimental method

The transwell culture chamber was used for this experiment with a haptoinvasion method (reference: Cancer Res., 47, 3239, (1987)). The lower side of a filter having a hole of 8.0 $\mu$m in diameter was coated with 5 $\mu$g of matrigel for the fabrication of matrigel/FN filter. Human adenosarcoma tissue cell (HT1080), treated in the intestinal flora metabolite of ginseng saponin in a concentration of 1–1000 $\mu$M at 37° C. for 30 minutes, was charged to the upper side of each filter with $1 \times 10^5$ cells/100 $\mu$L. Then, said filters were added to 24-well plate having 600 $\mu$L of MEM medium supplemented with 0.1% bovine serum albumin and them cultured for 4-hour cultivation. After completing the cultivation, cells were fixed with methanol and stained with hematoxylin, a tissue staining agent. Following the removal of cells at the upper side with a cotton pole, cells infiltrating into the lower side were counted under microscope.

b) Experimental results

As shown in table 4, the experimental results revealed that each intestinal metabolite of ginseng saponin exhibited more potent inhibitory activity of extravasation than RGDS peptide (under development from Glycomed Co.:Cancer Res., 49, 3815 (1989)), a control group and among them, 50% extravasation-inhibitory concentration of compound K showed a potent activity in a low concentration of 3.2 $\mu$M.

TABLE 4

Inhibition on the extravasation of basement membrane
by intestinal flora metabolites of ginseng saponin

|  | Concentration ($\mu$M) | No. of infiltrated cancer cell/field | Inhibition rate (%) |
|---|---|---|---|
| Control |  | 118 ± 8 |  |
| RGDS peptide | 4000 | 61 ± 9 | 48 |
| Compound K | 1 | 73 ± 4 | 38 |
|  | $ED_{50}$ = 3.2 |  | 50 |
|  | 10 | 45 ± 9 | 62 |
|  | 100 | 0 | 100 |
| Control |  | 117 ± 9 |  |
| RGDS peptide | 4000 | 51 ± 10 | 56 |
| Compound Y | 1 | 125 ± 7 |  |
|  | 10 | 92 ± 11 | 21 |
|  | $ED_{50}$ = 31 |  | 50 |
|  | 100 | 24 ± 2 | 62 |
|  | 1000 | 0 | 100 |
| Control |  | 117 ± 9 |  |
| RGDS peptide | 4000 | 51 ± 10 | 56 |
| ginsenoside Mc | 1 | 114 ± 12 | 3 |

TABLE 4-continued

Inhibition on the extravasation of basement membrane by intestinal flora metabolites of ginseng saponin

|  | Concentration ($\mu$M) | No. of infiltrated cancer cell/field | Inhibition rate (%) |
| --- | --- | --- | --- |
|  | $ED_{50}$ = 7.6 |  | 50 |
|  | 10 | 44 ± 7 | 62 |
|  | 100 | 3 ± 1 | 97 |
|  | 1000 | 0 | 100 |
| Control |  | 97 ± 8 |  |
| RGDS peptide | 4000 | 49 ± 4 | 49 |
| 20(S)-protopanaxatriol | 1 | 103 ± 14 |  |
|  | 10 | 93 ± 7 | 4 |
|  | $ED_{50}$ = 48 |  | 50 |
|  | 100 | 18 ± 4 | 81 |
|  | 1000 | 1 ± 1 | 99 |

From the aforementioned results, it is noted that intestinal flora metabolites of ginseng saponin, such as compound K, compound Y, 20(S)-protopanaxatriol including ginsenoside Mc of this invention, are novel types of potential anticancer agent since they have immunopotentiating actions including inhibitory actions on the vascularization of tumors and extravasation of cancer cells.

The toxicity of ginsenoside Mc, a novel compound of this invention, is nearly negligible in some animal experiments with rats and mice and the products' stability of each preparation based upon each formulation example is quite effective.

What is claimed is:
1. A compound of the formula:

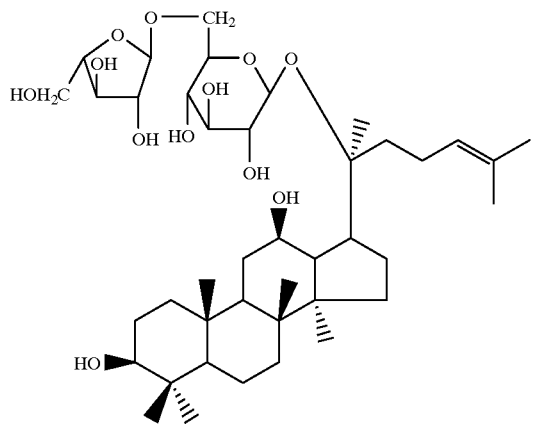

2. A pharmaceutical composition comprising a pharmaceutically effective amount of a compound of claim 1 and a pharmaceutically acceptable carrier.

3. The pharmaceutical composition of claim 2, wherein the active ingredient is administered in a dosage of between 1.0–50 mg/Kg/day.

4. The pharmaceutical composition of claim 3, wherein the form of the composition is selected from the group consisting of an orally administrable form, an injectable form, and an externally applicable form.

5. The pharmaceutical composition of claim 4, wherein the orally administrable form is selected from the group consisting of a tablet, a powder, a suspension, an emulsion, a capsule, a granule, a troche, a pill, a liquid, a spirit, a syrup and a limonade.

6. The pharmaceutical composition of claim 4, wherein the injectable form is selected from the group consisting of a liquid, a suspension and a solution.

7. The pharmaceutical composition of claim 4, wherein the externally applicable form is selected from the group consisting of an ointment, a liquid, a powder, a plaster, a suppository, an aerosol, a liniment, a lotion, an enema and an emulsion.

8. A pharmaceutical composition comprising a pharmaceutically effective amount of a compound selected from the group consisting of 20-0-[$\beta$-D-glucopyranosyl]-20(S)-protopanaxadiol (compound K), 20-0-[$\alpha$-L-arabinopyranosyl (1$\rightarrow$6)-$\beta$-D-glycopyranosyl]-20(S)-protopanaxadiol(compound Y), and 20(S)-protopanaxatriol, together with one or more pharmaceutically acceptable carriers.

9. The pharmaceutical composition of claim 8, wherein the active ingredient is 20-0-[$\beta$-D-glucopyranosyl]-20(S)-protopanaxadiol (compound K).

10. The pharmaceutical composition of claim 8, wherein the active ingredient is 20-0-[$\alpha$-L-arabinopyranosyl(1$\rightarrow$6)-$\beta$-D-glycopyranosyl]-20(S)-protopanaxadiol (compound Y).

11. The pharmaceutical composition of claim 8, wherein the active ingredient is 20(S)-protopanaxatriol.

12. The pharmaceutical composition of claim 8, wherein the active ingredient is administered in a dosage of between 1.0–50.0 mg/Kg/day.

13. The pharmaceutical composition of claim 12, wherein the form of the composition is selected from the group consisting of an orally administrable form, an injectable form, and an externally applicable form.

14. The pharmaceutical composition of claim 13, wherein the orally administrable form is selected from the group consisting of a tablet, a powder, a suspension, an emulsion, a capsule, a granule, a troche, a pill, a liquid, a spirit, a syrup and a limonade.

15. The pharmaceutical composition of claim 13, wherein the injectable form is selected from the group consisting of a liquid, a suspension and a solution.

16. The pharmaceutical composition of claim 13, wherein the externally applicable form is selected from the group consisting of an ointment, a liquid, a powder, a plaster, a suppository, an aerosol, a liniment, a lotion, an enema and an emulsion.

* * * * *

UNITED STATES PATENT AND TRADEMARK OFFICE
CERTIFICATE OF CORRECTION

PATENT NO.  : 5,919,770
DATED       : July 6, 1999
INVENTOR(S) : Hasegawa HIDEO et al It is certified that error appears in the above-identified patent and that said Letters Patent is hereby corrected as shown below:

Claim 3, line 3, replace with 1.0-50 mg/60Kg/day.
Claim 12, line 3, replace with 1.0-50 mg/60Kg/day.

Signed and Sealed this

Seventh Day of December, 1999

Attest:

Q. TODD DICKINSON

*Attesting Officer*          *Acting Commissioner of Patents and Trademarks*